United States Patent [19]

Oda et al.

[11] 4,093,797

[45] June 6, 1978

[54] NOVEL AMINOCYCLITOLS AND PROCESS FOR PRODUCTION THEREOF

[75] Inventors: Takeshi Oda, Kodaira; Toshito Mori; Takashi Yamaguchi, both of Higashimurayama, all of Japan

[73] Assignee: Kowa Company Ltd., Nagoya, Japan

[21] Appl. No.: 718,770

[22] Filed: Aug. 30, 1976

[30] Foreign Application Priority Data

Sept. 3, 1975 Japan .................. 50/106031

[51] Int. Cl.$^2$ ............................................. C07H 15/22
[52] U.S. Cl. ........................ 536/17; 424/180; 536/4
[58] Field of Search ......................................... 536/17

[56] References Cited

U.S. PATENT DOCUMENTS

| | | | |
|---|---|---|---|
| 3,872,080 | 3/1975 | Daniels | 536/17 |
| 3,878,193 | 4/1975 | Reimann | 536/17 |
| 3,928,317 | 12/1975 | Kirby et al. | 536/17 |
| 3,960,833 | 6/1976 | Naito et al. | 536/17 |

FOREIGN PATENT DOCUMENTS 10,235   2/1976   Japan.

*Primary Examiner*—Johnnie R. Brown
*Attorney, Agent, or Firm*—Sherman & Shalloway

[57] ABSTRACT

Novel $\beta$-D-ribofuranosyl (1 $\rightarrow$ 5), O-[$\alpha$-D-2-amino(or 2-acylamino)-2, 3-dideoxy-glucopyranosyl (1 $\rightarrow$ 4) ] 1, 3-diamino (or 1, 3-diacylamino)-1, 2, 3-trideoxy-myoinositols and their acid salts. These compounds are useful either as antibiotics or as intermediates for their synthesis. The compound can be produced by treating an O-$\alpha$-L-2, 6-diacylamino-2, 6-dideoxyidopyranosyl (1 $\rightarrow$ 3), $\beta$-D-ribofuranosyl (1 $\rightarrow$ 5), O-[$\alpha$-D-2-acylamino-2, 3-dideoxy-glucopyranosyl (1 $\rightarrow$ 4)] 1, 3-diacylamino-1, 2, 3-trideoxy-myoinositol with periodic acid or its salts, reacting the resulting compound with an amine, and optionally deacylating the product.

2 Claims, No Drawings

NOVEL AMINOCYCLITOLS AND PROCESS FOR PRODUCTION THEREOF

This invention relates to novel aminocyclitols which have antibiotic activity and are also noteworthy as intermediates for the synthesis of other antibiotics, and to a process for their production.

More specifically, the invention relates to β-D-ribofuranosyl (1 → 5), O-[α-D-2-amino (or 2-acylamino)-2,3-dideoxy-glucopyranosyl (1 → 4)] 1,3-diamino (or diacylamino)-1,2,3-trideoxy-myoinositols of the following formula

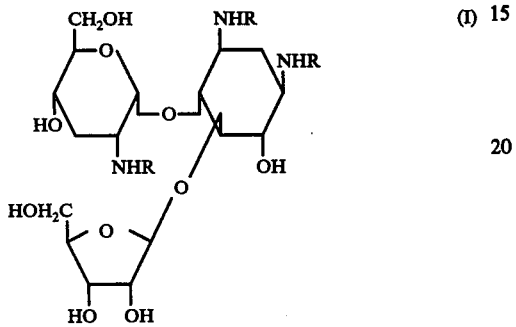

wherein R represents a hydrogen atom or an acyl group, and their acid salts; and also to a process for preparing them.

An antibiotic substance named "Quintomycin" which falls under the aminocyclitols and is produced by an Actinomyces, *Streptomyces lividus*, or its mutant, and its preparation are described in detail in U.S. Pat. Nos. 3,870,698 and 3,891,506. This Quintomycin is now called "Lividomycin".

O-α-L-2,6-diamino-2,6-dideoxy-idopyranosyl (1 → 3), β-D-ribofuranosyl (1 → 5), O-[α-D-2-amino-2,3-dideoxyglucopyranosyl (1 → 4)] 1,3-diamino-1,2,3-trideoxy-myoinositol of the following formula

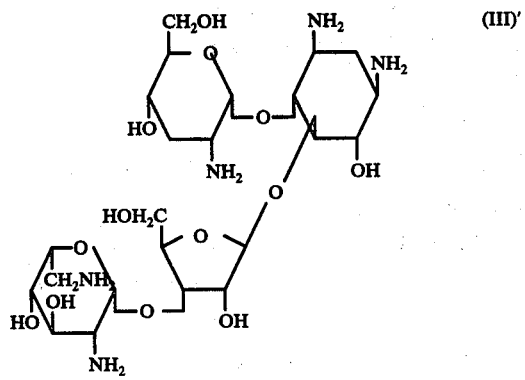

which is referred to as Quintomycin D in the specifications of the above U.S. patents is now called Lividomycin B.

O-α-D-mannopyranosyl (1 → 4), α-L-2,6-diamino-2,6-dideoxy-idopyranosyl (1 → 3), β-D-ribofuranosyl (1 – 5), O-[α-D-2-amino-2,3-dideoxy-glucopyranosyl (1 → 4)] 1,3-diamino-1,2,3-trideoxy-myoinositol of the following formula

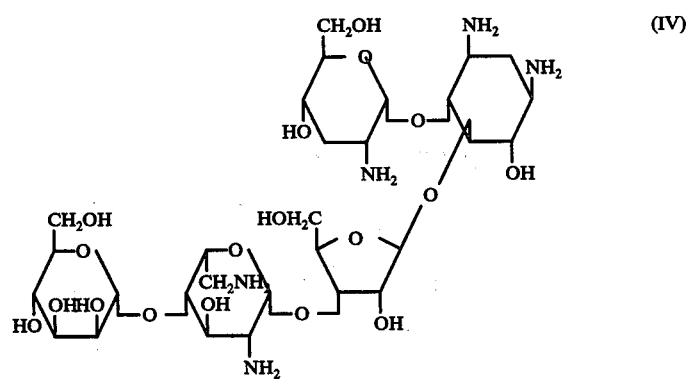

which is referred to as Quintomycin B in the specifications of the above U.S. patents is now called Lividomycin A.

Lividomycin B can be produced not only by the fermentation method disclosed in the above U.S. patents, but also by a method which comprises treating an acylation product of Lividomycin A (e.g., an N-acylation product obtained by acetylating Lividomycin A to protect its —NH₂ in the form of —NH—acetyl) with periodic acid or its salts to decompose the terminal mannose to form a dialdehyde compound, and reacting it with phenyl hydrazine, or first reducing the dialdehyde compound and then reacting it with a weak acid. The detailed of the method of producing Lividomycin B from Lividomycin A are described in Japanese Patent Publication No. 10235/76 published Apr. 2, 1976.

We have now found that the β-D-ribofuranosyl (1 → 5), O-[α-D-2-amino(or 2-acylamino)-2,3-dideoxy-glucopyranosyl (1 → 4)] 1,3-diamino(or diacylamino)-1,2,3-trideoxy-myoinositols of formula (I) are useful as intermediates for preparing other antibiotics can be produced easily in good yields and purities.

Accordingly, an object of this invention is to provide novel aminocyclitols of formula (I) which are useful as antibiotics and intermediates for antibiotics.

Another object of this invention is to provide a process for producing the novel aminocyclitols of formula (I).

These and other objects of the invention along with its advantages will become more apparent from the following description.

The compounds of formula (I) in accordance with this invention can be obtained easily in good yields and purities by treating Lividomycin B (Quintomycin D) obtained by the methods described in the above cited two U.S. patents, or an N-acylation product, e.g., an N-acetylation product, of Lividomycin B obtained by treating Lividomycin A (Quintomycin B) of formula (IV) (obtained by the methods of the two U.S. patents) by the method disclosed in Japanese Patent Publication No. 10235/76, with periodic acid or its salts; reacting the resulting compound with an amine; and optionally deacylating the product.

This reaction can be schematically shown as follows:

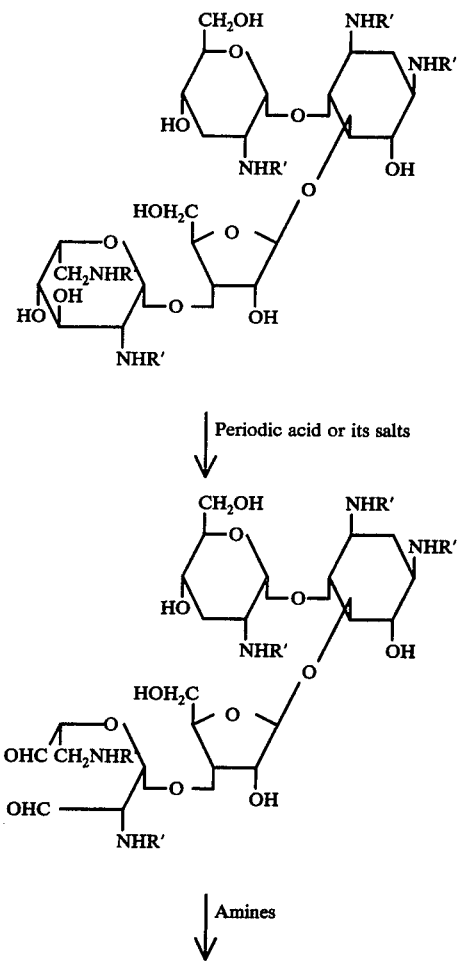

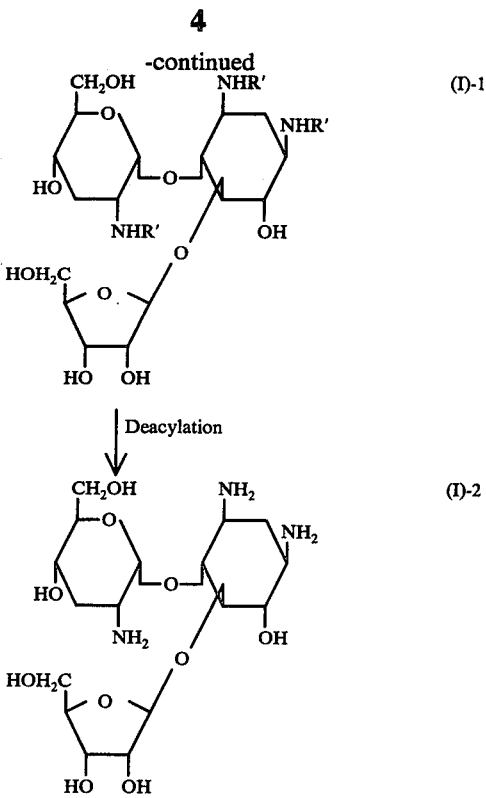

An N-acylation product of Lividomycin B of formula (III), for example, penta-N-acetyl Lividomycin B, can be obtained easily by acylating Lividomycin B. The acylation may be carried out in an acetic anhydride/methanol solution at room temperature for several hours with stirring. Optionally the reaction can be carried out at an elevated temperature. For example, the acetic anhydride/methanol solution is added to Lividomycin B, and the mixture is stirred at room temperature for several hours. The reaction proceeds rapidly by heating.

According to the process of this invention, the resulting N-acyl-Lividomycin B is treated with periodic acid or its salts in an amount equal to, or larger than, the amount of the compound of formula (III), for example, up to about 2 times the amount of the compound of formula (III), thereby to convert it to the compound of formula (II). Preferably, the reaction is carried out in a solvent such as water, lower alcohols (e.g., methanol or ethanol), or mixtures of water and the alcohols. The reaction proceeds at room temperature and ends in about 5 to 30 hours. The reaction time can be shortened, however, by carrying out the reaction at an elevated temperature. Generally, temperatures of from about 5° to about 50° C. can be employed. Preferably, the reaction should be carried out in the absence of light in order to avoid side-reactions. Examples of the periodic acid salts are alkali metal salts such as sodium or potassium salts, and alkaline earth metal salts such as calcium or barium salts.

As a result of the treatment with periodic acid or its salts, ring opening occurs between carbon atoms at the 3- and 4-positions of the neosamine B moiety to afford a dialdehyde compound of formula (II). After the reaction, the dialdehyde compound of formula (II) may be separated and recovered by concentrating the reaction mixture to dryness and extracting it with methanol; or if desired decomposing the excess of periodic acid or a salt thereof with, for example, ethylene glycol, precipitating the free iodine in the form of a salt using a salt-forming compound such as lead acetate, and removing the precipitate. Alternatively, the reaction mixture may be concentrated to dryness, and the dried product extracted with a lower alcohol such as methanol or ethanol to obtain the dialdehyde of formula (II), followed by adding a nonpolar solvent such as ether to precipitate it.

The resulting dialdehyde compound of formula (II) is then reacted with an amine to afford the β-D-ribofuranosyl (1 → 5), O-[α-D-2-acylamino-2,3-dideoxy-glucopyranosyl (1 → 4)] 1,3-diacylamino-1,2,3-trideoxy-myoinositol. Examples of amines that can be used to remove the ring-opened neosamine B moiety of the compound of formula (II) are phenyl hydrazine and triethylamine. The reaction can be carried out using, for example, phenyl hydrazine, in the same solvent as used in the preparation of the compound of formula (II) from the compound of formula (III). The reaction temperature is preferably from room temperature to about 200° C., more preferably from about 80° C. to about 120° C. Usually, the reaction time is about 1 to about 10 hours. Preferably, the reaction is carried out in the copresence of acids so as to make the reaction proceed smoothly. The use of organic acids gives especially favorable results. Lower fatty acids are particularly preferred for this purpose. In the case of using triethylamine, the compound of formula (I)-1 can be obtained by performing the reaction in a solvent, preferably a lower alcohol such as methanol, at room temperature for about 1 to 10 hours. The reaction can be performed also under heat, and temperatures from room temperature to about 60° C. are frequently used.

The amount of the amine can be freely chosen, and usually, it is 2 to 5 times the amount of the compound of formula (II).

The compound of formula (I)-1 obtained can be separated and purified by column chromatography using a column of silica gel, alumina, or magnesium silicate, etc. As an adsorbing solvent, a mixture of chloroform and methanol, acetone or ethyl acetate can be used. The same mixed solvent can also be used as an eluting solvent. As the adsorbing solvent, the preferred volume ratio of chloroform to the other solvent is about 1 to 0.5, and as the eluting solvent, the preferred volume ratio of chloroform to the other solvent is about 1 to 0.5.

Compounds of formula (I)-1 in which R' is an acyl group can be deacylated, as required, by a known means to easily convert them to compounds of formula (I)-1 in which R' is a hydrogen atom [i.e., formula (I)-2]. The compounds of formula (I)-2 have antibiotic activity. The deacylation reaction can be carried out, for example, by an alkali treatment which involves heating the compound under reflux in an aqueous solution of an alkali hydroxide. It is preferred that the separation of the compound of formula (I)-2 from the reaction mixture and its purification should also be performed by column-chromatographic techniques using a column of a cation exchange resin such as Amberlite IRC-50 and IR-120 (Rohm & Haas Co.), CM-Sephadex X-25 and C-50 (Pharmacia Co.) and Diaion WK-11 (Mitsubishi Chemical K.K.). Water can be used as an adsorbing solvent. Examples of suitable eluting solvents are aqueous alkali solutions such as sodium hydroxide, potassium hydroxide and ammonia solutions, the aqueous solution of ammonia being especially preferred.

The compound of formula (I)-2 can be readily converted to an acid salt by adding a mineral acid such as sulfuric acid or hydrochloric acid, carbonic acid, or a lower fatty acid such as acetic acid or propionic acid, or a higher fatty acid such as stearic acid or palmitic acid.

The following Examples illustrate the present invention further.

EXAMPLE 1

2.0 g of penta-N-acetyl-Lividomycin B of formula (III) was dissolved in water, and 800 mg of sodium periodate was added. The mixture was stirred overnight at room temperature in the absence of light. After the reaction, ethylene glycol was added to decompose the unreacted sodium periodate, and the reaction mixture was evaporated to dryness at reduced pressure. The residue was extracted with methanol, and ether was added to the extract. The precipitate was collected by filtration. Thus, 2.0 g of a dialdehyde compound of formula (II) was obtained.

To 1.7 g of the dialdehyde compound was added 35 ml of a 10% triethylamine/methanol solution, and the mixture was stirred at 25° C. for 4 hours. The mixture was then concentrated, and the residue was dissolved in a chloroform/methanol (2/1). It was allowed to be adsorbed to a column of silica gel, and eluted with chloroform/methanol (2/1). Concentration of the eluate afforded 950 mg of a compound of formula (I) in which R is an acetyl group. The physico-chemical properties of the product were as follows:

Melting point: 173° - 176° C. (decomp.)

NMR (CD$_3$OD): δ 2.01 (9H, s NHCOCH$_3$) 5.29 (1H, J=1 Hz, d) 5.50 (1H, J=2 Hz, d)

Elemental analysis value for $C_{23}H_{39}N_3O_{13} \cdot \frac{1}{2}$ H$_2$O:

|  | C | H | N |
|---|---|---|---|
| Calculated (%) | 48.08 | 7.02 | 7.31 |
| Found (%) | 48.06 | 7.01 | 7.41 |

Specific rotation: $[\alpha]_D^{26}$ + 49° (C 0.5, MeOH)

900 mg of the resulting acetylation product was heated under reflux for 5 hours in 22 ml of 4N sodium hydroxide. The reaction mixture was neutralized with hydrochloric acid, and the salt was removed by Amberlite IRC-50 (NH$_4$$^+$ type, an ion exchange resin produced by Rohm & Mass Co.). The solution was then caused to be adsorbed to 76 ml of CM Sephadex C-25 (NH$_4$$^+$ type, an ion exchange resin made by Pharmacia Co.). It was eluted using a concentration gradient of water (500 ml) - 0.2N ammonium hydroxide (500 ml) (each fraction measured 12 ml). The 43rd to 58th fractions, which had antibacterial activity, were collected and lyophilized to afford 580 mg of a compound of formula (I) in which R is a hydrogen atom. The physico-chemical properties of the product were as follows:

Melting point: 167.0° - 170.0° C. (decomp.)

$[\alpha]_D^{26}$ + 74° (C 0.5, H$_2$O).

IR (KBr) cm$^{-1}$: 3400 (—NH$_2$, —OH), 2920 (—CH$_2$—).

NMR (D$_2$O): δ 5.23 (1H, J=1 Hz, d), 5.33 (1H, m)

Dilute sulfuric acid was added to an aqueous solution of the resulting product, and the pH of the mixture was adjusted to about 5. It was then lyophilized to afford a sulfate of the compound (I) as a white powder. The physico-chemical properties of the sulfate were as follows:

Melting point: 170° - 174° C. (decomp.)

Elemental analysis value for $C_{17}H_{33}N_3O_{10} \cdot 3/2\ H_2SO_4 \cdot 2H_2O$:

|  | C | H | N | S |
|---|---|---|---|---|
| Calculated (%) | 32.80 | 6.47 | 6.75 | 7.72 |
| Found (%) | 32.67 | 6.10 | 6.91 | 8.02 |

Specific rotation: $[\alpha]_D^{26} + 30°$ (C 0.8, $H_2O$)

EXAMPLE 2

160 mg of the dialdehyde compound obtained in Example 1 was dissolved in water, and 1.1 ml of phenyl hydrazine and 0.5 ml of acetic acid were added. The mixture was heated at 100° C. for 3 hours. The reaction mixture was washed with chloroform, and allowed to be adsorbed to a mixed ion exchange resin consisting of Amberlite IRC-120 ($H^+$ type) and Amberlite IRA-411 (OH-type), followed by elution with water. The eluate was concentrated to afford 95 mg of a compound of formula (I) in which R is an acetyl group.

What we claim is:

1. β-D-ribofuranosyl (1→5), O-[α-D-2-amino (or 2-acylamino)-2,3-dideoxy-glucopyranosyl (1→4)] 1,3-diamino (or 1,3-diacylamino)-1,2,3-trideoxy-myoinositol of the following formula

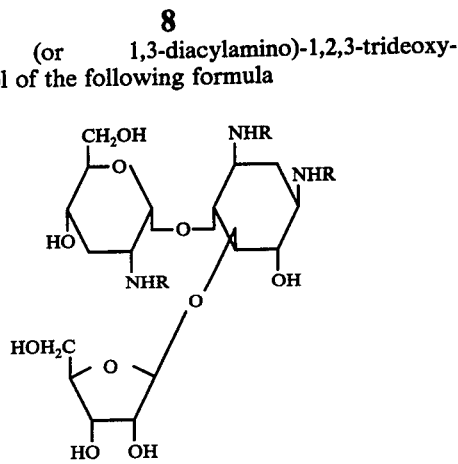

wherein R represents a member selected from the group consisting of hydrogen, acetyl, and an acid salt of said acetyl.

2. An acid salt of the compound of claim 1 in which the acid is a member selected from the group consisting of sulfuric, hydrochloric, carbonic, acetic, propionic, stearic or palmitic acid.

* * * * *